United States Patent [19]

Stevens et al.

[11] Patent Number: 5,619,143

[45] Date of Patent: Apr. 8, 1997

[54] MICROWAVE SCANNING APPARATUS

[75] Inventors: Thomas J. Stevens, Highett; Robert H. Leicester, Beaumaris, both of Australia

[73] Assignee: Commonwealth Scientific and Industrial Research Organisation, Campbell, Australia

[21] Appl. No.: 999,732

[22] Filed: Nov. 30, 1992

Related U.S. Application Data

[63] Continuation of Ser. No. 741,450, filed as PCT/AU90/00046, Feb. 9, 1990, published as WO90/09578, Aug. 23, 1990, abandoned.

[30] Foreign Application Priority Data

Feb. 14, 1989 [AU] Australia .................................. PJ2736

[51] Int. Cl.$^6$ .................................................. G01N 22/02
[52] U.S. Cl. ...................... 324/639; 324/647; 324/640; 73/159
[58] Field of Search .................... 73/159, 160; 324/631, 324/636, 637, 639, 648

[56] References Cited

U.S. PATENT DOCUMENTS

| | | |
|---|---|---|
| 2,798,197 | 7/1957 | Thurston . |
| 2,844,789 | 7/1958 | Allen ........................................ 324/631 |
| 3,810,005 | 5/1974 | Bennion et al. . |
| 4,087,746 | 5/1978 | Kanae ....................................... 324/631 |
| 4,123,702 | 10/1978 | Kinanen ................................... 324/639 |
| 4,500,835 | 2/1985 | Heikkila .................................. 324/637 |
| 4,514,680 | 4/1985 | Heikkila .................................. 324/631 |
| 4,710,700 | 12/1987 | Osaki ...................................... 324/636 |
| 4,818,930 | 4/1989 | Flemming ................................ 324/632 |
| 4,885,527 | 12/1989 | Lacombe .................................. 324/636 |

FOREIGN PATENT DOCUMENTS

| | | |
|---|---|---|
| 160488 | 11/1985 | European Pat. Off. . |
| 623145 | 8/1978 | U.S.S.R. . |
| 726475 | 4/1980 | U.S.S.R. . |
| 813211 | 3/1981 | U.S.S.R. . |
| 1195231 | 5/1984 | U.S.S.R. . |
| 1439375 | 6/1976 | United Kingdom . |
| 1489554 | 10/1977 | United Kingdom . |
| 1560591 | 2/1980 | United Kingdom . |
| 1564194 | 4/1980 | United Kingdom . |

OTHER PUBLICATIONS

Microwave Electromagnetic Nondestructive Testing of Wood, Ray J. King, Symposium on Non–Destructive Testing of Wood, 4th Vancouver 1978, Wash. State University Proceedings pp. 121–134.

Microwave Electromagnetic Non–Destructive Testing of Wood in Real–Time, Y. Yen, 1981, University Microfilms International, Michigan.

Oil and Water Content Measurement of Sandstone Cores Using Microwave Measurement Techniques, IEEE Transactions on Instrumentation & Measurement, Volu. IM–35, No. 4, Dec. 1986, pp. 630–637.

Primary Examiner—Kenneth A. Wieder
Assistant Examiner—Jose M. Solis
Attorney, Agent, or Firm—Sughrue, Mion, Zinn, Macpeak & Seas

[57] ABSTRACT

A method and apparatus for detecting grain direction in wood by means of microwave radiation. A sample of timber is exposed to a polarized microwave beam emitted by a transmitter (11). A polarized receiver (12) evaluates the microwave energy that has been affected by the timber. The receiver and transmitter polarization planes are locked at either 0 or 90 degrees respect to each other. Both are rotated synchronously and the received energy is plotted versus angle. The energy maximum or minimum gives indication of the grain direction in the timber sample under evaluation.

12 Claims, 2 Drawing Sheets

5,619,143

MICROWAVE SCANNING APPARATUS

This is a Continuation of application Ser. No. 07/741,450, filed as PCT/AU90/00046, Feb. 9, 1990, published as WO90/09578, Aug. 23, 1990, now abandoned.

TECHNICAL FIELD

The present invention relates to apparatus for testing samples using microwave radiation and, in particular, provides apparatus suitable for high-speed on-line machine testing of sawn timber.

Although the invention is described below with reference to a particular application, it is to be understood that the invention is susceptible of wider application, its application to the testing of timber being merely exemplary of its potential uses.

BACKGROUND ART

Timber, as a natural biological material, shows considerable variation in its properties. This variation occurs both from one tree to another and within a single board of timber. Given the widespread use of timber as a structural component, it is important economically to be able to test it quickly and reliably for sorting into groups with guaranteed engineering properties and/or appearance. The use of microwave radiation for the testing of timber meets these requirements of economy, speed and reliability—being non-destructive and allowing non-physically contacting test apparatus to be built which is particularly suitable for automated real time monitoring of timber in high speed saw milling operations.

Furthermore, microwave radiation can be used, reliably, to determine various parameters affecting the physical and structural properties of wood. For example, the loss, phase shift and depolarisation of microwaves transmitted through wood (which is a strongly anisotropic substance) can be measured to infer moisture content, density, presence of knots, presence of pith, slope of grain and parallelism of fibres. A theoretical background for such measurements is given in the papers "Microwave Electromagnetic Non-destructive Testing of Wood in Real Time" Y. Yen 1981, University Microfilms International, Michigan, USA; and "Microwave Electromagnetic Non-Destructive Testing of Wood" by R. J. King, Proceedings of Symposium on Non-destructive Testing of Wood, Vancouver 1978, pages 121–134.

Known microwave apparatus for testing wood, as disclosed in the above two papers, involves an arrangement wherein a microwave signal is transmitted through a timber sample to be scattered by a relatively complex mechanically spun, electrically modulated dipole. A portion of the resultant scattered signal propagates back through the timber and is received by the same antenna from which the original signal was transmitted for mixing with a reference signal and subsequent processing. Measurements of loss, depolarisation and phase shift are made and the characteristics of the timber sample such as density, moisture content, grain direction, parallelism of fibres and presence of pith are derived therefrom.

U.S. Pat. No. 4,123,702 and GB patent No. 1489554 disclose systems wherein knots in timber are detected by transmitting frequency modulated microwave radiation through the timber and detecting phase shifts in the transmitted microwaves—the phase shifts being caused by the presence of knots. GB patent No. 1564194 discloses knot detection apparatus requiring at least one pair of transmitting antennae and in which 180° phase shifted microwave signals are transmitted through or reflected from mutually adjacent areas of the timber and are then compared, a null output indicating the absence of knots. GB 1564194 also discloses detection of deviations of the timber grain direction by measuring phase and/or amplitude changes due to depolarisation of the 180° out of phase incident signals (the direction of polarisation of the incident signals being different). GB patent No. 1560591 discloses a similar system in which there is a single transmitting antenna and at least one pair of receiving antennae. The apparatus disclosed in U.S. Pat. No. 3,810,005 also depends on a comparison between microwave radiation measured at two adjacent positions, after its transmission through the timber. This system requires the presence of two detectors.

DISCLOSURE OF THE INVENTION

An object of the present invention is to provide alternative apparatus which allows much greater flexibility in the use of polarised microwave radiation for measurement purposes.

Accordingly, there is provided apparatus for testing a sample, such as timber, comprising means for supplying plane polarised microwave radiation to a sample testing zone and means for detecting microwave radiation received from the testing zone, the apparatus including first means to adjustably rotate (as defined herein) the plane of polarisation of the microwave radiation that is supplied to the testing zone a second adjustable polarisation rotating means is positioned in front of the detecting means to receive the microwave radiation from the testing zone, the planes of polarisation of each polarisation rotating means being independently adjustable, whereby the degree of rotation of the polarisation rotating means and/or the amplitude or phase shift of the received microwave radiation provides a measure of the properties of a sample within the zone.

As used herein and in the claims, the words "adjustably rotate" or similar words having the same import, mean that the plane of polarisation is positionable or settable at any desired angle of rotation.

The sample may be moving relative to the apparatus and preferably the microwave radiation passes through a sample as the sample passes relatively through the testing zone.

With this preferred arrangement the angle of anisotropic properties of a sample, for example the grain direction in a timber sample, is easily measured by setting the polarisation rotating means such that they are locked at 90° cross polarised positions. The rotating means may then be adjusted as a pair until the detecting means indicates the position of minimum depolarisation, that is the position at which the detector gives a minimum output. At this position the polarisation angle of the incident microwave radiation will be aligned with or be at 90° to the direction of the major anisotropic development in the sample, for example the grain direction in a timber sample. It should be noted that the apparatus of the invention when used in this way is not dependent on and therefore does not require any amplitude calibration.

The presence and magnitude of irregularities in a sample may also be indicated with the rotating means locked at 90° cross polarised positions and set such that the incident microwave radiation is minimally depolarised by the sample. In the absence of irregularities a zero or minimal signal will be indicated at the detector, however irregularities in the sample (for example the presence of a knot in timber) will cause depolarisation of the microwave radiation which will be indicated by the presence of a signal at the detector. A measure of the magnitude of the irregularity will be indicated by the time span of the signal. The presence of irregularities may also be indicated with the rotating means aligned in polarisation—in this case variations in the normal signal at the detector are indicative of the presence of irregularities in a sample passing through the testing zone. Again, these methods of use of the apparatus do not require any amplitude calibration.

The above described apparatus may comprise one arm of a bridge circuit having a reference arm to which a portion of the supplied plane polarised microwave radiation is transmitted, the detecting means providing a comparative measure of the microwave radiation in the reference and sample test arms of the circuit.

Preferably the reference arm of the bridge circuit includes phase and amplitude adjustment means.

A bridge circuit as above described allows measurement of parameters that may be used to determine properties such as density, moisture content and the degree of anisotropic development (for example the presence of pith in timber) in a sample. When used in a bridge circuit, the rotating means of the apparatus of the invention are aligned in polarisation and the bridge circuit is brought to a balanced condition by way of the phase and amplitude adjustment means in the reference arm—the degree of adjustment that is required being a measure of the attenuation and phase shift in the incident microwave radiation caused by the sample. The attenuation and phase shift caused by the sample is indicative of the density and moisture content of that sample. Additionally, the attenuation and phase shift, by adjustment of the polarisation rotating means, can be measured at different angles of orientation of the plane of polarisation of the incident radiation to the sample. Changes in the measurements between the different angles are indicative of the degree of anisotrophic development in the sample. This method can also be used with the non-bridge form of the invention, described previously to determine parameters to indicate degree of amisotropic development. Of course, the above described measurements involving a bridge circuit require calibration of the measurement apparatus.

It will be appreciated that apparatus in accordance with the invention allows the angle of the plane of polarisation of the incident microwave radiation to be readily varied with respect to the sample, thereby providing much greater flexibility in the modes of use and possible measurement regimes of the apparatus.

BRIEF DESCRIPTION OF THE DRAWINGS

An example of apparatus embodying the invention will now be described with reference to the accompanying drawings in which.

BEST MODES FOR CARRYING OUT THE INVENTION

Figure 1:
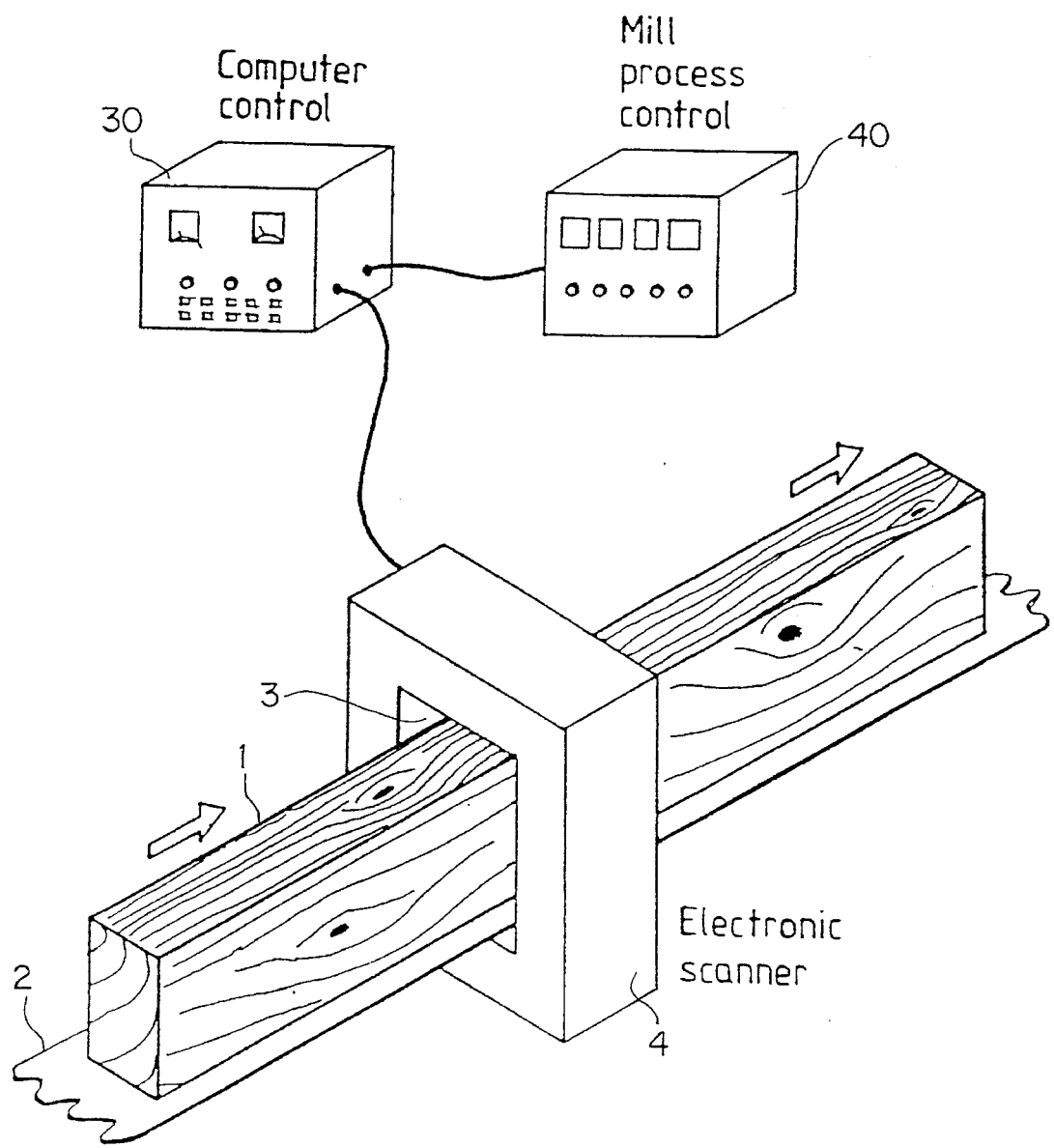
FIG. 1 shows a typical arrangement of apparatus according to the invention in a timber saw milling environment.

FIG. 1 shows a sample of sawn timber 1 being carried by a conveyor 2 through a testing zone 3 defined by an electronic scanner 4. The electronic scanner comprises the circuitry shown in FIG. 2. The electronic scanner in FIG. 1 is shown as under the control of a computer 30, but this is not essential. The computer may be linked, as shown, to the process control apparatus 40 of the saw mill to thereby control upstream operations and/or downstream acceptance/rejection operations on particular boards, so as to optimise the mill's output. Typically, sawn timber will be carried by conveyor 2 at speeds between about 2–5 meters per second.

The invention encompasses a situation where the scanner is moved and the sample is stationary; that is, the only requirement is that there be relative movement between the scanner and the sample. The invention, however, is not limited to measuring the properties of relatively moving samples, that is, it may also be used with stationary samples.

Figure 2:
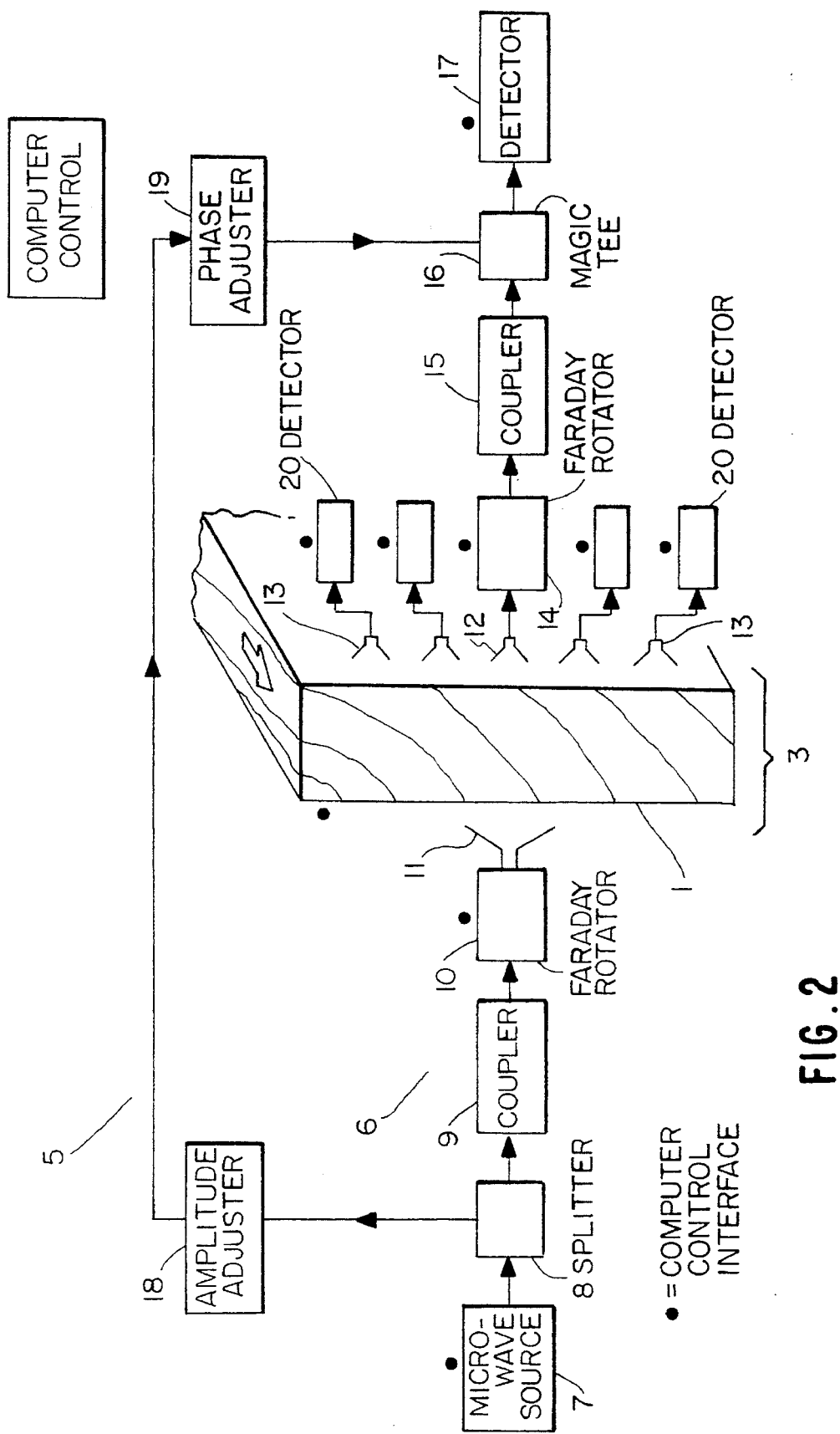
FIG. 2 is a diagramatic representation of a microwave bridge circuit that includes the invention.

FIG. 2 illustrates the microwave bridge circuit of the electronic scanner. The bridge circuit comprises a reference arm 5 and sample test arm 6. The test arm includes a testing zone 3 through which a sample 1 passes. Unmodulated and plane polarised microwave radiation, typically in the range of 30–100 mW and having a frequency of 10 GHz, is generated by microwave source 7 and transmitted to signal splitter 8 where it is split into a portion that is transmitted through the test arm 6 and a portion that is transmitted through the reference arm 5. The test arm signal is coupled to a polarisation rotating means 10 via unidirectional coupler 9. The polarisation rotating means may be a Faraday rotator by means of which the polarisation plane of the input signal is adjustably rotatable to any desired angle. The signal passes from the rotating means 10 to transmitting horn 11 for transmission through sample 1. The radiation transmitted through the sample, which may be attenuated, phase shifted and depolarised depending on the properties of the sample, is received by horn 12 and passed to a second polarisation rotating means 14, for example a Faraday rotator, and to detector 17 via another coupler 15 and magic tee 16. The reference arm 5 includes signal amplitude adjustment means 18 and phase adjustment means 19. As shown, the apparatus may include other receiving horns 13 coupled to detectors 20 which enable localisation of defects, such as knots. Alternatively a bank of small receiving horns 13 may be coupled to Faraday rotator 14. Other possible circuit structures include the use of single wide transmitting and receiving horns or banks of small transmitting and receiving horns.

The sample test arm may include phase and amplitude compensation means (not shown) for disturbances caused by the Faraday rotators. All components may also be under computer control and programmable, as indicated schematically in FIG. 2.

Microwave engineers will readily appreciate and be able to construct the above apparatus on the basis of the description that is provided, it being understood that the specific components may take any of the various suitable forms as will be within the knowledge of an appropriate addressee.

The operation of the apparatus, whether under programmed computer control or manual, admits of a wide degree of flexibility and is particularly suitable for a saw mill environment. In operation, the reference arm 5 may be switched off and, as described above, the Faraday rotators 10 and 14 locked at 90° cross polarised positions. Adjustment of the rotators as a pair to give the minimum signal at detector 17 enables the grain direction of the timber to be determined. Detection of irregularities in the sample is possible with the rotators locked in a 90° cross polarised position, or locked in alignment, by observing the magnitude of the output signal at detector 17 as a sample passes through zone 3. When used in this way, calibration of the apparatus is not necessary.

In the bridge mode of operation, the rotators 10 and 14 are locked in alignment and density and moisture content are determinable from the amplitude and phase adjustments, 18 and 19, required to bring the bridge to a balanced condition. In this mode of operation pith detection is also possible from comparison of the measurements of attenuation and phase shift taken for varying angles of the polarisation of the incident radiation with respect to the sample. Calibration of the apparatus is required when the bridge circuit mode of operation is used.

The circuit may include supplementary elements to enhance its speed of operation. For example, a step modulated source (plus or minus 0.03% in frequency) allows ready identification of sense or direction for phase balance.

Additional detectors sensing 1% of the signal in each arm of the bridge at the main detector allows ready identification of large steps to amplitude balance. A quadrature detector at the main detector station allows ready identification of large steps to phase balance.

Those skilled in the art will appreciate that the invention described herein is susceptible to variations and modifications other than those specifically described. It is therefore to be understood that the invention includes all such variations and modifications which fall within its spirit and scope.

We claim:

1. A method of determining the grain direction in a sample of timber comprising:

supplying plane polarised microwave radiation to the sample from a first polarisation rotating means and detecting plane polarised radiation received from the sample after passage through a second polarisation rotating means, characterised by the steps of
   i) locking the planes of polarisation of the first and second polarisation rotating means at a set angle of 0° or 90° with respect to each other,
   ii) rotatably adjusting the locked together planes of polarisation of the first and second polarisation rotating means as a pair until
      a) the detector indicates a minimum signal for the case where the planes of polarisation are set at 90° with respect to each other, or
      b) the detector indicates a maximum signal for the case where the planes of polarisation are set at 0° with respect to each other,
   iii) determining the grain direction of the timber sample from the angle of adjustment of the first or second polarisation rotating means at the point which provides the said minimum or maximum signal.

2. A method as claimed in claim 1 including the further steps of
   i) maintaining the locked together first and second polarisation rotating means at the angle of adjustment which provides the minimum or maximum signal at the detector while moving the timber sample relative to the supplied plane polarised microwave radiation, and
   ii) monitoring the level of the signal at the detector whereby a change in said signal level indicates the presence of an irregularity in the timber sample.

3. A method as claimed in claim 2 wherein the monitoring step includes determining the time span of any change in the signal level indicative of the presence of an irregularity, and determining from said time span and relative speed of the timber a measurement of the size of the irregularity.

4. A method as claimed in claim 1 in which the planes of polarisation of the first and second polarisation rotating means are locked at 0° with respect to each other, and including the further steps of
   i) splitting a portion of the plane polarised microwave radiation from that which is supplied to the first polarisation rotating means, and coupling the split portion of the plane polarised microwave radiation to the detector,
   ii) while maintaining the locked together first and second polarisation rotating means at the angle which provides a maximum signal at the detector, adjusting the amplitude and phase of the split off portion until the detector indicates a minimum signal, whereby the change in amplitude and phase of the split off portion needed to bring the detector to a minimum value provides a measure of the attenuation and phase shift induced in the microwave radiation that passes through the timber sample.

5. Apparatus for determining grain direction in a sample of timber, comprising:

means for supplying plane polarised microwave radiation to a sample of timber;

means for detecting microwave radiation received from the sample;

a first polarisation rotating means for rotating the plane of polarisation of the microwave radiation that is supplied to the sample and in which the plane of polarisation is selectively lockable at any desired angle; and a second polarisation rotating means, positioned in front of the detecting means to receive the microwave radiation from the sample, for rotating the plane of polarisation of the received microwave radiation, the plane of polarisation of the second polarisation rotating means also being selectively lockable at any desired angle;

wherein the planes of polarisation of the first and second polarisation rotating means are lockable at a set angle relative to each other and are rotatable as a locked pair in locked together orientations; and wherein the detecting means provides an output signal having a magnitude dependent upon the angle between the two planes of polarisation and the grain direction of the sample of timber, whereby the grain direction is determinable from said output signal and degree of rotational adjustment of the locked pair of polarisation rotating means.

6. Apparatus as claimed in claim 5 wherein the first and second polarisation rotating means are electronic signal rotators.

7. Apparatus as claimed in claim 6 wherein the first and second polarisation rotating means are Faraday rotators.

8. Apparatus as claimed in claim 5 including means to transmit a portion of the supplied plane polarized microwave radiation to the detector via a path that does not pass through the sample or the first and second polarisation rotating means.

9. Apparatus as claimed in claim 8 wherein the said path includes phase and amplitude adjustment means.

10. Apparatus as claimed in claim 5 wherein the means for supplying plane polarised radiation and means for detecting microwave radiation are positioned on opposite sides of the sample such that the detecting means receives microwave radiation that has been transmitted through a sample.

11. Apparatus as claimed in claim 10 wherein a sample and the apparatus are moveable relative to each other.

12. Apparatus as claimed in claim 11 including means to convey a sample through the testing zone.

* * * * *